US008706182B2

(12) United States Patent  
Yamashita (10) Patent No.: US 8,706,182 B2  
(45) Date of Patent: Apr. 22, 2014

(54) BIOSIGNAL DETECTING ELECTRODE AND BIOSIGNAL DETECTING DEVICE EQUIPPED THEREWITH

(75) Inventor: Shiko Yamashita, Tokyo (JP)

(73) Assignee: Sony Corporation, Tokyo (JP)

( * ) Notice: Subject to any disclaimer, the term of this patent is extended or adjusted under 35 U.S.C. 154(b) by 17 days.

(21) Appl. No.: 13/285,630

(22) Filed: Oct. 31, 2011

(65) Prior Publication Data

US 2012/0136233 A1    May 31, 2012

(30) Foreign Application Priority Data

Nov. 25, 2010  (JP) ................................. 2010-262978

(51) Int. Cl.
*A61B 5/0448* (2006.01)
*A61B 5/04* (2006.01)
*A61B 5/0476* (2006.01)
*A61B 5/0478* (2006.01)

(52) U.S. Cl.
USPC ............ 600/383; 600/372; 600/393; 600/544

(58) Field of Classification Search
USPC ................. 600/372, 378, 382–384, 388, 390, 600/392–393, 395–396, 544–545; 607/115, 607/118

See application file for complete search history.

(56) References Cited

U.S. PATENT DOCUMENTS

| | | | |
|---|---|---|---|
| 5,038,782 A * | 8/1991 | Gevins et al. ................. | 600/383 |
| 6,510,333 B1 * | 1/2003 | Licata et al. .................. | 600/383 |
| 2007/0238945 A1 * | 10/2007 | Delic et al. ..................... | 600/383 |
| 2009/0030298 A1 * | 1/2009 | Matthews et al. ............. | 600/372 |

FOREIGN PATENT DOCUMENTS

EP     0 232 102      8/1987

* cited by examiner

*Primary Examiner* — Linda Dvorak  
*Assistant Examiner* — Brian M Antiskay  
(74) *Attorney, Agent, or Firm* — K&L Gates LLP

(57) ABSTRACT

Disclosed herein is a biosignal detecting electrode which includes a rotary part which is rotatably attached on a brace mountable on a living body and has a first side that joins to the brace and a second side opposite to the first side, and a plurality of electrode terminals attached to the rotary part in such a way that they obliquely project from the second side of the rotary part.

9 Claims, 7 Drawing Sheets

BIOSIGNAL DETECTING ELECTRODE AND BIOSIGNAL DETECTING DEVICE EQUIPPED THEREWITH

CROSS REFERENCES TO RELATED APPLICATIONS

The present application claims priority to Japanese Priority Patent Application JP 2010-262978 filed in the Japan Patent Office on Nov. 25, 2010, the entire content of which is hereby incorporated by reference.

BACKGROUND

The present application relates to a biosignal detecting electrode and a biosignal detecting device equipped therewith, the biosignal detecting electrode is designed to detect biosignals when brought into contact with the site of a human or animal body where there exists hair.

It is common practice to analyze electrical signals (or biosignals), such as electroencepharogram and electromyogram, in order to grasp a human's or animal's health state. Measurement of such biosignals is usually accomplished by means of a measuring electrode brought into contact with the site of a human body for measurement. If the site for measurement is a hair-growing one, there will be an instance in which the hair existing between the skin and the measuring electrode prevents electrical contact between them.

Under these circumstances, there has been developed a device for measuring biosignals which is equipped with an electrode to acquire biosignals at the site where there exists hair. For example, Japanese Patent Laid-open No. Sho 62-231621 (The upper right portion of the third page, and FIG. 7) (hereinafter referred to as Patent Document 1) discloses "Head set for measurement of electroencepharogram" which is equipped with an electrode of bundled silver wires. The bundled silver wires are impregnated with an electrolytic solution, and the electrode of bundled silver wires is brought into contact with the patient's head.

SUMMARY

The electrode of bundled silver wires disclosed in Patent Document 1 suffers the disadvantage of causing pain to the patient when it is brought into contact with the patient's head. Moreover, the tightly bundled silver wires prevent the electrode from complete contact with the scalp in the presence of hair.

The foregoing motivated the present application, which is intended to provide a biosignal detecting electrode that can be brought into contact with the skin without being hindered by hair.

According to one embodiment, the biosignal detecting electrode is composed of a rotary part and a plurality of electrode terminals.

The rotary part is rotatably attached to a brace that can be mounted on a living body. It has a first side attached to the brace and a second side opposite to the first side.

The electrode terminals project obliquely from the second side of the rotary part.

The foregoing structure permits the electrode terminals, which project obliquely with respect to the second side, to move hair aside and come into good contact with the skin as the rotary part rotates.

The rotary part is capable of rotation on the axis which is a straight line passing though the centers of the first and second sides. The electrode terminals are arranged rotationally symmetrical with respect to the axis. In addition, the electrode terminals are exactly or approximately uniform in length from the first side to their tips.

The electrode terminals constructed as mentioned above come into complete contact with the skin because they have their tips evenly positioned and have their contact pressure evenly distributed.

The electrode terminals may be formed from a liquid holding material impregnated with an electrolytic solution.

With the foregoing structure, the electrode terminals achieve good electrical contact with the skin because they permit the electrolytic solution to ooze out of them when they come into mechanical contact with the skin.

The electrode terminals may be formed from any elastic material.

The resulting electrode terminals deform in conformity with the shape of the skin, thereby coming into close contact with the skin.

According to one embodiment, the biosignal detecting device is composed of an attaching brace, a rotary part, and electrode terminals.

The attaching brace is intended to attach the biosignal detecting device to the patient's body.

The rotary part is rotatably mounted on the attaching brace. It has a first side fixed to the attaching brace and a second side opposite to the first side.

The electrode terminals project obliquely from the second side of the rotary part The electrode terminals projecting obliquely from the second side move hair aside for their complete contact with the skin.

The biosignal detecting device mentioned above may additionally have a driving mechanism to turn the rotary part and a control unit to control the driving mechanism in response to the contact resistance of the electrode terminals.

The control unit determines the degree of contact between the electrode terminals and the skin and controls the rotation of the rotary part according to the result of determination. This automatically ensures good contact between the electrode terminals and the skin.

As mentioned above, the present disclosure provides a biosignal detecting electrode which can be brought into contact with the skin, with hair moved aside.

Additional features and advantages are described herein, and will be apparent from the following Detailed Description and the figures.

DETAILED DESCRIPTION (The First Embodiment)

The following is a description of the first embodiment.
[Structure of the Biosignal Detecting Device]

Figure 1:
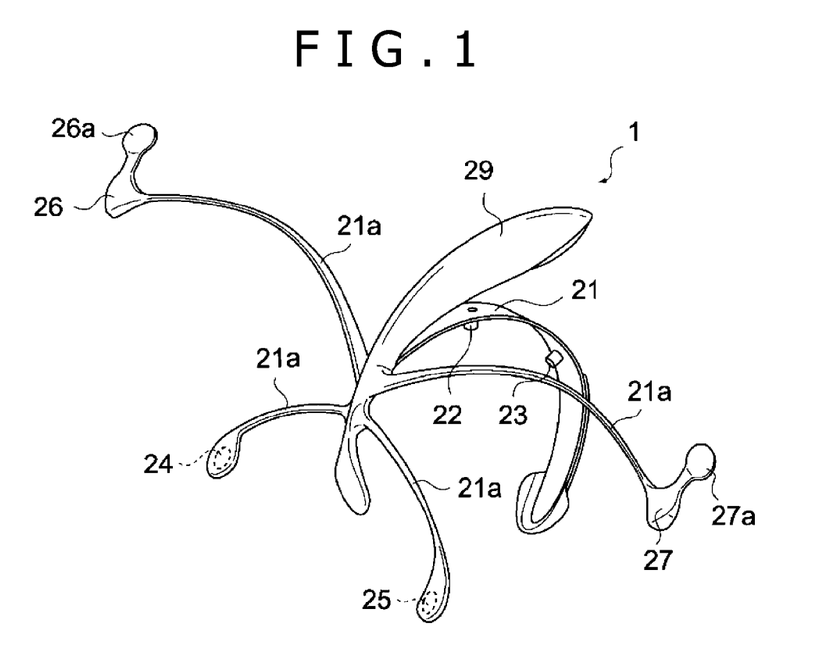
FIG. 1 is a perspective view showing the biosignal detecting device according to the first embodiment.

FIG. 1 is a perspective view showing the biosignal detecting device 1 according to the first embodiment.

The biosignal detecting device 1 has the head band 21 to be supported on the patient's head. To the head band 21 are connected the parietal electrode 22, the occipital electrode 23, the right electro-ocular electrode 24, the left electro-ocular electrode 25, the right reference electrode 26, the left reference electrode 27, and the enclosure 29.

The head band 21 is a member extending from the forehead to the parietal and occipital of the patient. It takes on an arched shape that fits to the patient's head. Moreover, the head band 21 holds the patient's head with its elastic force. The head band 21 has four arms 21a each supporting the right electro-ocular electrode 24, the left electro-ocular electrode 25, the right reference electrode 26, and the left reference electrode 27. The shape of the head band 21 may be properly varied The parietal electrode 22 comes into contact with the patient's parietal, and the occipital electrode 23 comes into contact with the patient's occipital. The parietal electrode 22 and the occipital electrode 23 are intended to measure the patient's electroencephalogram (EEG). Since they are placed on the patient's sites where there exist hair, it is necessary that they come into contact with the scalp directly (with hair moved aside) so that they effectively acquire the EEG. Their structure to achieve this object will be detailed later.

The right electro-ocular electrode 24 comes into contact with the patient's right temple, and it is a flat electrode made of conductive material. It is attached to the arm 21a extending from the head band 21 to the patient's right temple when the patient wears the biosignal detecting device 1. Similarly, the left electro-ocular electrode 25 comes into contact with the patient's left temple, and it is a flat electrode made of conductive material. It is attached to the arm 21a extending from the head band 21 to the patient's left temple when the patient wears the biosignal detecting device 1. The right electro-ocular electrode 24 and the left electro-ocular electrode 25 are intended to measure the patient's eye movement.

The right reference electrode 26 comes into contact with the back of the patient's earlobe, and it is a flat electrode made of conductive material. It is attached to the arm 21a extending from the head band 21 to the patient's right ear when the patient wears the biosignal detecting device 1. It has the earlobe holder 26a which holds the earlobe in conjunction with it as it is positioned on the front of the earlobe. Similarly, the left reference electrode 27 comes into contact with the back of the patient's earlobe, and it is a flat electrode made of conductive material. It is attached to the arm 21a extending from the head band 21 to the patient's left ear when the patient wears the biosignal detecting device 1. It has the earlobe holder 27a which holds the earlobe in conjunction with it as it is positioned on the front of the earlobe.

The enclosure 29 is attached to the head band 21 in such a way that it permits the patient to easily wear the biosignal detecting device 1. It contains electronic components such as processor, memory, and communication interface. The head band 21 and the arms 21a are provided with wiring (not shown) for connection with the electrodes and the electronic components.

[Structure of the Parietal Electrode and the Occipital Electrode]

The following is a detailed description of the parietal electrode 22 and the occipital electrode 23. Since these constituents are of the same structure, the description is limited to the former.

Figure 2:
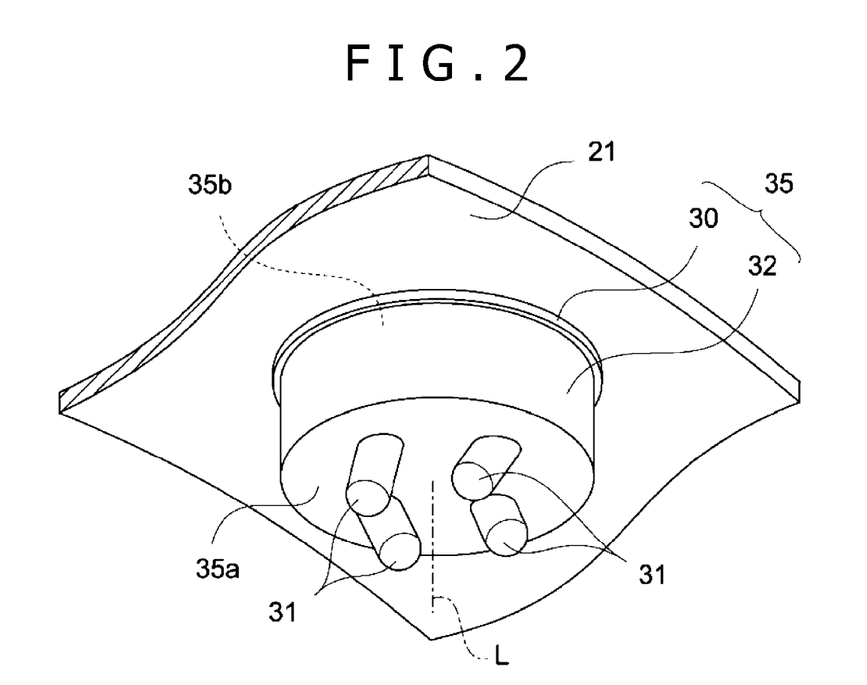
FIG. 2 is a perspective view showing the parietal electrode of the same biosignal detecting device as above.

FIG. 2 is a perspective view showing the structure of the parietal electrode 22.

Figure 3:
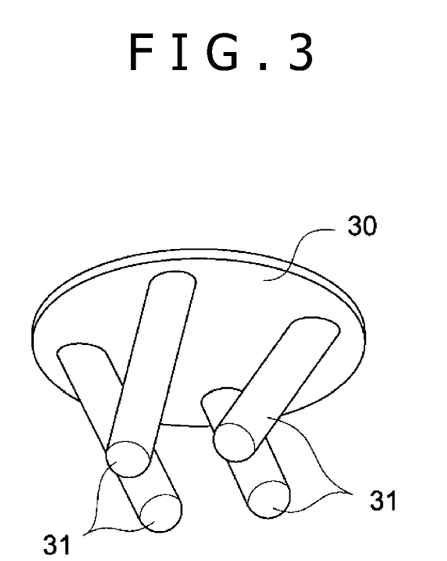
FIG. 3 is a perspective view showing the parietal electrode of the same biosignal detecting device as above, with the attaching brace removed.

The parietal electrode 22 is composed of the base 30, the four electrode terminals 31, and the support 32. The base 30 is connected to the head band 21. The electrode terminals 31 are mounted on the base 30. In addition, the support 32 on the base 30 partly covers the electrode terminals 31. FIG. 3 is a perspective view showing the parietal electrode 22, with the support 32 removed.

The base 30 is a flat member made of conductive material. It is rotatably supported on the head band 21, so that the parietal electrode 22 can be turned by the patient. Alternatively, the base 30 may be so designed as to be turned by a rotary drive (such as motor) or a mechanical power source, as mentioned later. As the base 30 turns relative to the head band 21, the parietal electrode 22 entirely turns relative to the head band 21. The base 30 has wiring (not shown) for connection with electronic components contained in the enclosure 29.

The support 32, which is fixed to the base 30, covers the electrode terminals 31 in such a way that at least the top of each electrode terminals 31 is exposed. It is formed from a flexible material such as polyurethane. It may take on any shape, such as cylinder and truncated cone.

The rotary part 35 is composed of the base 30 and the support 32. It turns, relative to the head band 21, together with the electrode terminals 31. It has the first side 35a (which is away from the head band 21) and the second side 35b (which is in contact with the head band 21). It turns around the axis which is the straight line connecting the center of the first side 35a and the center of the second side 35b. This line is represented by L in FIG. 2.

Figure 4A:
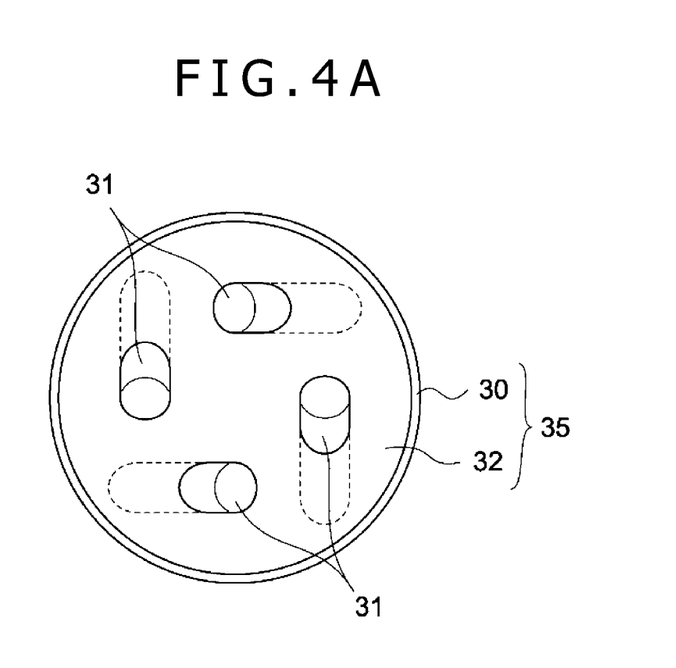
FIGS. 4A and 4B are a plan view and a side view, respectively, showing the structure of the electrode terminals of the parietal electrode of the same biosignal detecting device as above.
Figure 4B:
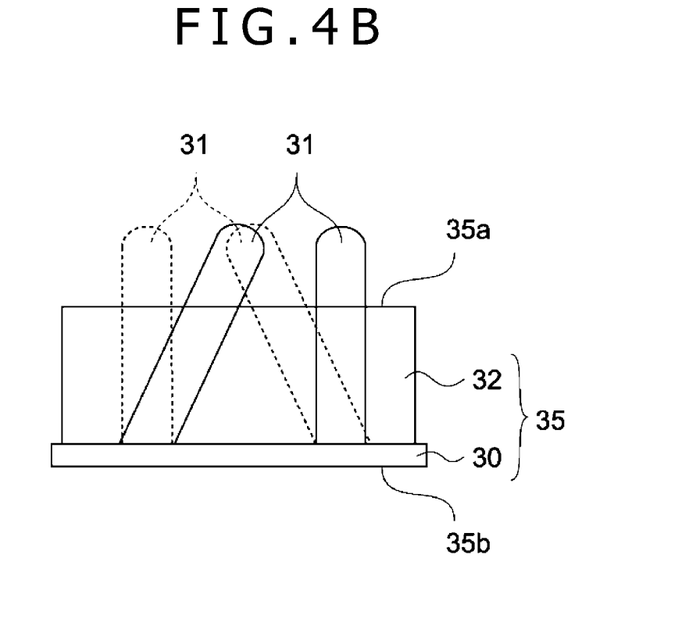

The electrode terminals 31 are rod-like members formed on the base 30. FIGS. 4A and 4B are a top view and a side view both showing the structure of the electrode terminals 31. There are four electrode terminals 31 in this embodiment; however, their number may be changed to three or five or more. The electrode terminals 31 are arranged (on the second side 35b) rotationally symmetrical with respect to the axis (or the line L)

To be more specific, the electrode terminals 31 are inclined at a certain angle toward the plane on which their tips are positioned. The direction of inclination may be the direction in which the parietal electrode 22 turns. Incidentally, the parietal electrode 22 may rotate in either clockwise and counterclockwise directions but the electrode terminals 31 should be inclined in only one direction.

The electrode terminals 31 are constructed such that they have exactly or approximately equal distances from the first side 35a to their tips. Owing to this structure, the electrode terminals 31 have their tips positioned uniformly on a plane and they receive stress evenly when the biosignal detecting device 1 is brought into contact with the patient's head. The fact that the electrode terminals 31 are inclined at the same angle keeps them in contact with the skin at approximately equal angles, which ensures their effective contact with the skin.

Figure 5:
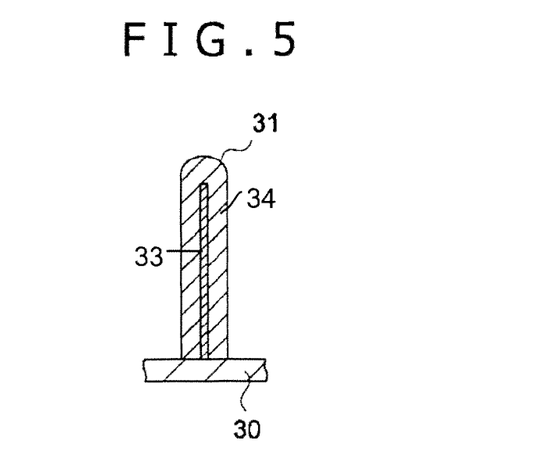
FIG. 5 is a sectional view showing the structure of one of the electrode terminals of the parietal electrode of the same biosignal detecting device as above.

The electrode terminal 31 is constructed as shown in FIG. 5 which is a sectional view. It is composed of the core 33 and the liquid holding part 34 covering the core 33. The core is made of stiff material such as metal and plastics. The liquid holding part 34 is made of any material capable of holding a liquid, such as felt, hard felt, felt pen refill, compressed fibrous plastics, and porous plastics. The liquid holding part 34 is impregnated with an electrolytic solution, such as a 30:70 mixture of physiological saline (containing 1% sodium chloride) and glycerin.

The electrode terminal 31 will have elasticity when the core 33 and the liquid holding part 34 are formed from adequate materials, so that it deforms in conformity with the object for its close contact.

The above-mentioned structure of the parietal electrode 22 is also applied to the occipital electrode 23. Both the parietal electrode 22 and the occipital electrode 23 are rotatably supported on the head band 21. They can be turned by the patient's hand or by a drive mechanism, such as motor (not shown), mounted on the head band 21. The drive mechanism may be one which produces a rotary movement when they are pushed against the head band 21.

Although the biosignal detecting device 1 according to this embodiment is originally designed to be mounted on the patient's head, it may also be mounted on any other sites where hair grows. Moreover, it may also be applied to any haired animals. In such cases, the biosignal detecting device 1 will be properly modified in shape according to the object to which it is applied. Incidentally, the biosignal detecting device 1 according to this embodiment will be applied satisfactorily to any hairless site of humans and animals.

[Functional Structure of the Biosignal Detecting Device]

Figure 6:
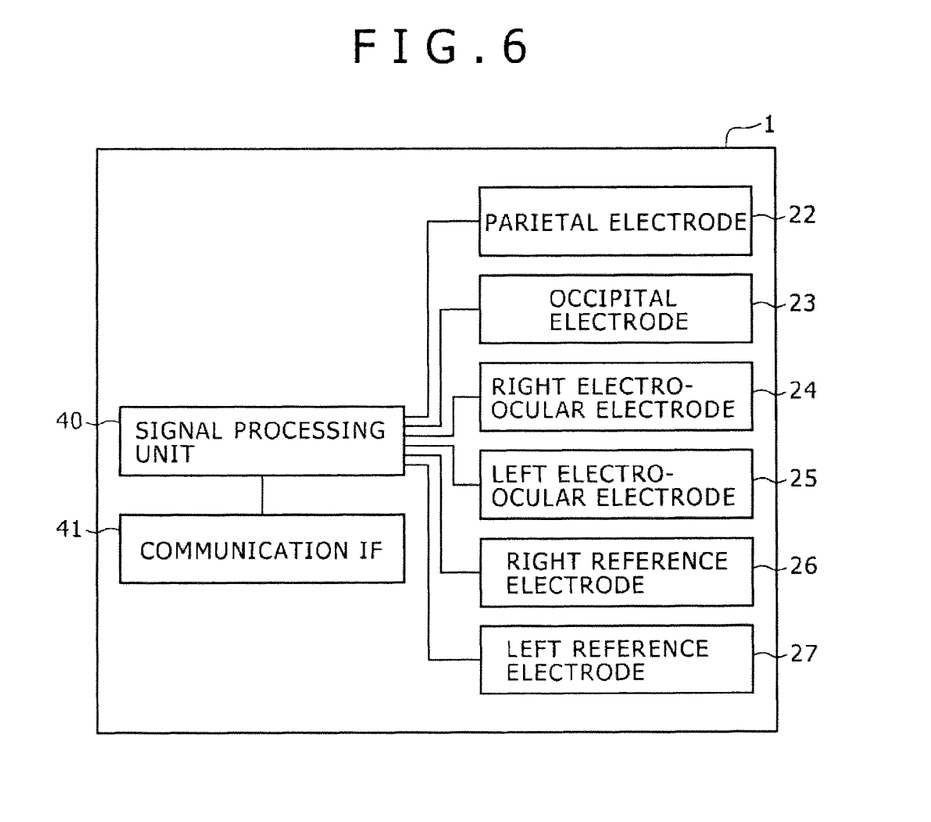
FIG. 6 is a block diagram illustrating the functional structure of the same biosignal detecting device as above.

FIG. 6 is a block diagram illustrating the functional structure of the biosignal detecting device 1.

As shown in FIG. 6, the biosignal detecting device 1 is composed of the parietal electrode 22, the occipital electrode 23, the right electro-ocular electrode 24, the left electro-ocular electrode 25, the right reference electrode 26, the left reference electrode 27, the signal processing unit 40, and the communication interface (IF) 41. The last two components are electronic components such as processor and memory, which are contained in the enclosure 29.

The parietal electrode 22, the occipital electrode 23, the right electro-ocular electrode 24, the left electro-ocular electrode 25, the right reference electrode 26, and the left reference electrode 27 are connected to the signal processing unit 40 through wiring attached to the head band 21. The signal processing unit 40 is connected to the communication IF 41.

Figure 7:
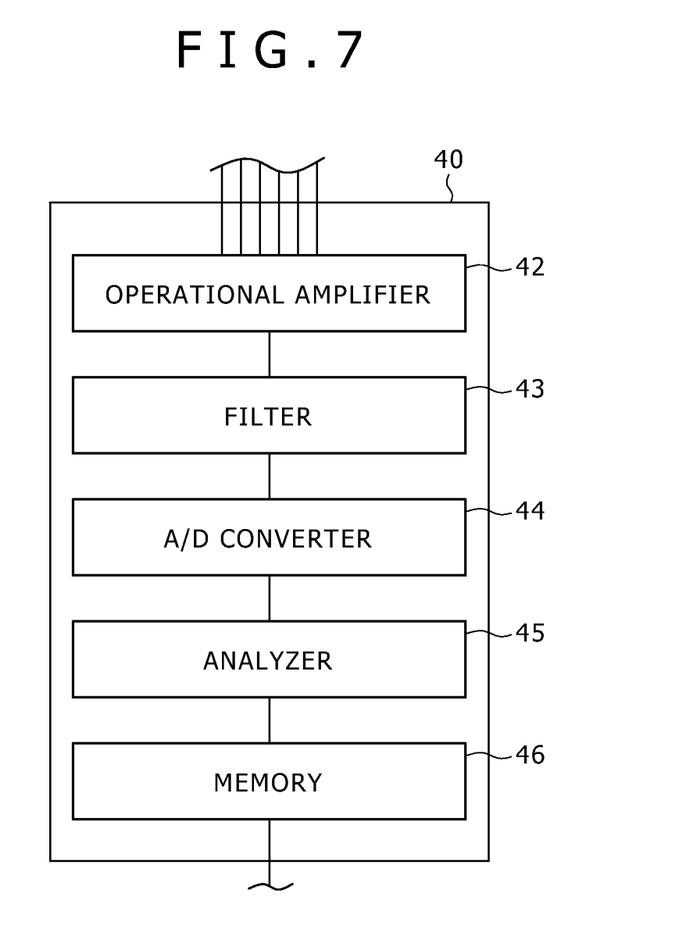
FIG. 7 is a block diagram illustrating the circuit structure of the signal processing unit of the biosignal detecting device.

The signal processing unit 40 is typically constructed as explained below. FIG. 7 is a block diagram illustrating the circuit structure of the signal processing unit 40. As shown in FIG. 7, the signal processing unit 40 is composed of the operational amplifier 42, the filter 43, the A/D converter 44, the analyzer 45, and the memory 46. The operational amplifier 42 is connected to the parietal electrode 22, the occipital electrode 23, the right electro-ocular electrode 24, the left electro-ocular electrode 25, the right reference electrode 26, and the left reference electrode 27. The operational amplifier 42, the filter 43, the A/D converter 44, the analyzer 45, the memory 46, and the communication IF 41 are sequentially connected one after another.

The operational amplifier 42 amplifies the potential difference (as biosignals) between the parietal electrode 22 and the right reference electrode 26 and between the occipital electrode 23 and the left reference electrode 27. The thus amplified biosignals are sent to the filter 43, which removes signal components outside the frequency band set up therein and the remaining signal components are sent to the A/D converter 44.

The frequency band which is set up in the filter 43 includes δ-wave (1 to 3 Hz), θ-wave (4 to 7 Hz), α-wave (8 to 13 Hz), β-wave (14 to 30 Hz), γ-wave (31 to 64 Hz), ω-wave (65 to 128 Hz), ρ-wave (129 to 512 Hz), and σ-wave (513 to 1024 Hz). All or part of these frequency bands are set up in the filter 43 as the frequency bands for measurement.

The A/D converter 44 converts biosignals into digital signals and sends the converted signals to the analyzer 45 which analyzes the biosignals. The analyzing process includes the determination of the sleep stage which denotes the degree of the patient's sleep. The analyzer 45 stores biosignals and analyzed results in the memory 46 and then sends them out through the communication IF 41.

The foregoing is a description of the structure of the biosignal detecting device 1. Incidentally, the structure mentioned above may have an additional electrode for acquisition of biosignals from the patient's site other than mentioned above.

[Action of the Biosignal Detecting Device]

The biosignal detecting device 1 is attached to the patient for its operation. It may be used not only for humans but also for animals (especially haired ones). During its operation, the parietal electrode 22 and the occipital electrode 23 rotate while being pressed against the patient's head. This rotation may be achieved by the patient or the drive mechanism attached to the biosignal detecting device.

The parietal electrode 22 and the occipital electrode 23, both in rotary motion, cause their terminals 31 to move aside hair so that they come into direct contact with the scalp. The rotary motion may be one turn (or more) or half turn. The electrode terminals 31 may obliquely move hair aside for their easy contact with the skin. Moreover, they come into contact with the scalp without causing pain to it because they are made of elastic material, and they achieve good electrical contact with the scalp because they are impregnated with an electrolytic solution.

Described above is the way in which the parietal electrode 22 and the occipital electrode 23 achieve their contact with the patient's scalp. The right electro-ocular electrode 24 and the left electro-ocular electrode 25 come into direct contact with the patient's hairless skin. Each electrode acquires biosignals and sends them to the signal processing unit 40, which processes them and sends out the processed signals to external devices through the communication IF 41.

(The Second Embodiment)

The following is a description of the second embodiment. Incidentally, identical structures in the first and second embodiments are denoted by identical reference symbols without repeated explanation.

[Functional Structure of the Biosignal Detecting Device]

Figure 8:
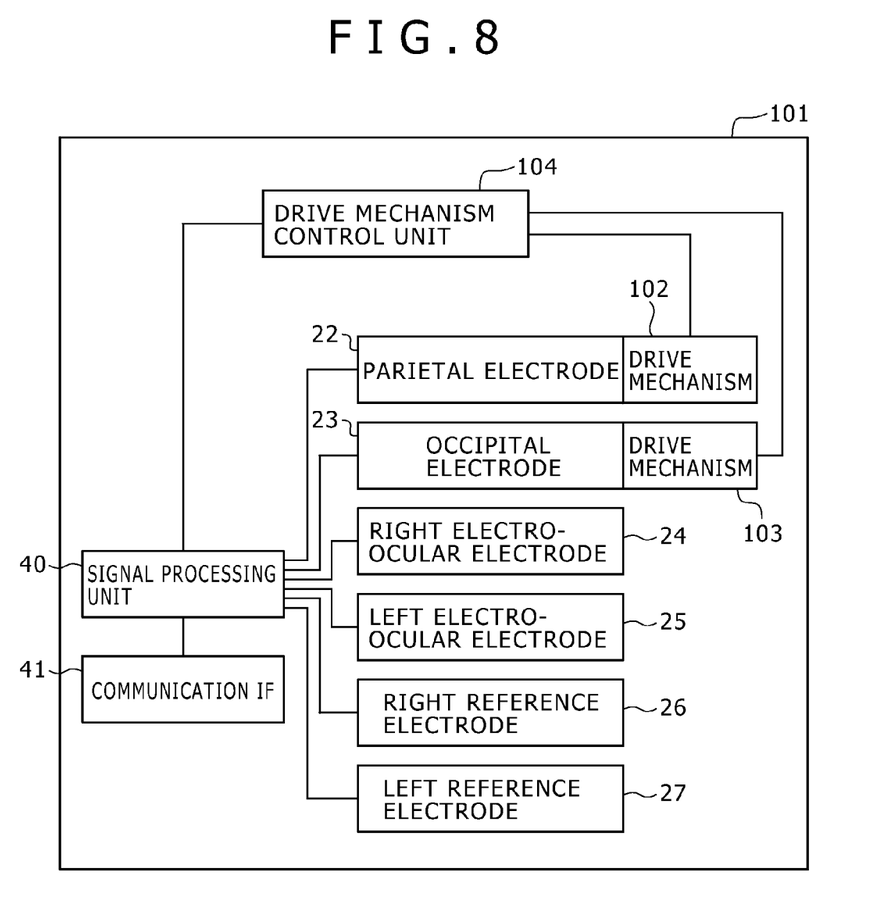
FIG. 8 is a block diagram illustrating the functional structure of the biosignal detecting device according to the second embodiment.

FIG. 8 is a block diagram illustrating the functional structure of the biosignal detecting device according to the second embodiment.

As shown in FIG. 8, the biosignal detecting device 101 is basically of the same structure but additionally has the drive mechanism 102 to rotate the parietal electrode 22, the drive mechanism 103 to rotate the occipital electrode 23, and the drive mechanism control unit 104 for their control, which is connected to the signal processing unit 40 and also to the drive mechanisms 102 and 103.

The drive mechanism 102, which may be a motor, causes the parietal electrode 22 to rotate relative to the head band 21. Likewise, the drive mechanism 103, which may be a motor, causes the occipital electrode 23 to rotate relative to the head band 21. The drive mechanism control unit 104 controls electric power to be applied to the drive mechanisms 102 and 103, thereby controlling the rotation of the parietal electrode 22 and the occipital electrode 23. It may rely for its function on the electronic components, such as processor, contained in the enclosure 29.

[Action of the Biosignal Detecting Device]

Figure 9:
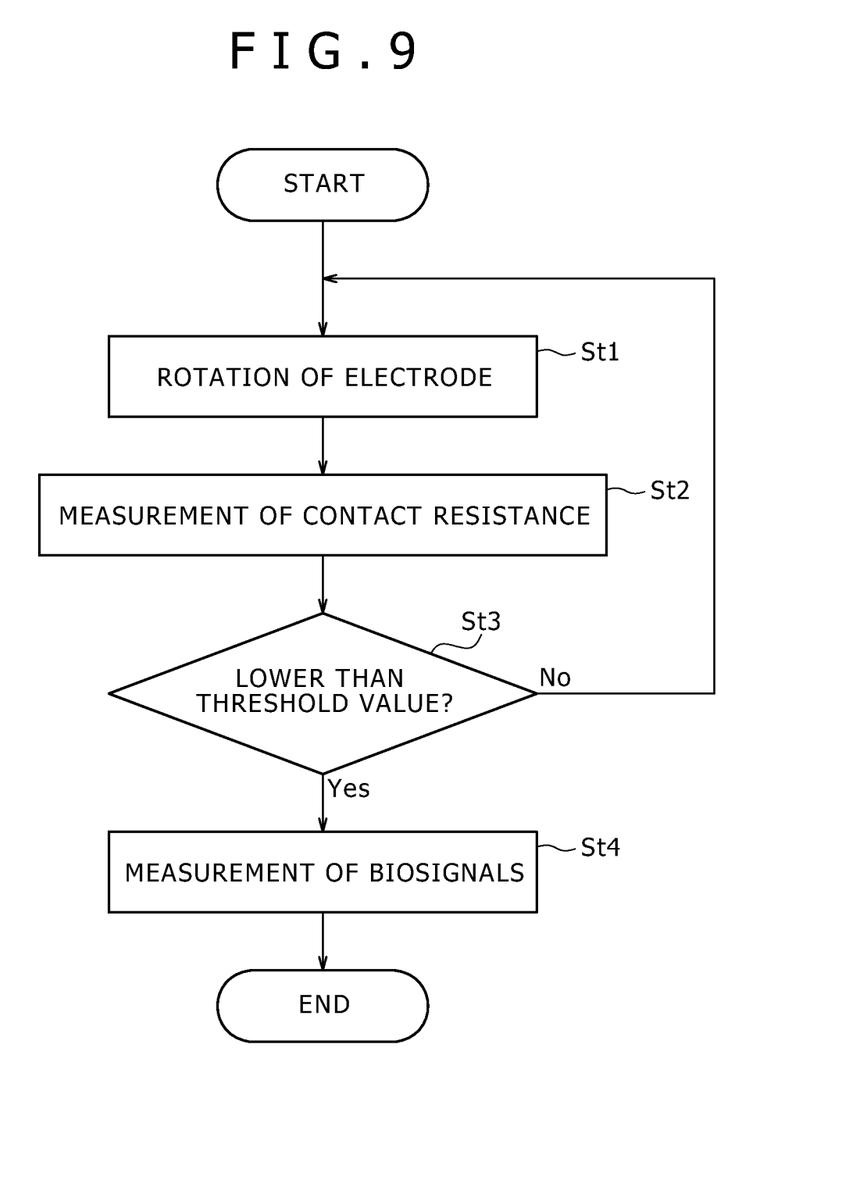
FIG. 9 is a flow chart showing the action of the same biosignal detecting device as above.

FIG. 9 is a flow chart showing the action of the biosignal detecting device 101. In Step St1, the drive mechanism control unit 104 causes the drive mechanisms 102 and 103 to rotate through a prescribed angle, with the biosignal detecting device 101 mounted on the patient's head.

In Step St2, the drive mechanism control unit 104 measures the contact resistance of the parietal electrode 22 and the occipital electrode 23. The contact resistance may be measured by the fall-off-potential method, for example. In Step St3, comparison is made between the thus measured contact resistance and the previously established threshold value. If the result of comparison is "Yes" or the former is smaller than the latter, Step St3 continues to Step St4. This result suggests that the terminals 31 of the parietal electrode 22 and the occipital electrode 23 are in good contact with the patient's scalp. In Step St4, the biosignal detecting device 101 measures biosignals in the same way as in the first embodiment.

If the result of comparison in Step St3 is "No" or the contact resistance is larger than the threshold value, the drive mechanism control unit 104 determines that the terminals 31 of the parietal electrode 22 and the occipital electrode 23 are not in good contact with the patient's scalp. In this case, the flow returns to Step St1 so that the drive mechanism control unit 104 causes the drive mechanisms 102 and 103 to rotate again. And subsequent steps St2 and St3 are repeated so that the contact resistance of the parietal electrode 22 and the occipital electrode 23 is measured and the rotation of the parietal electrode 22 and the occipital electrode 23 is repeated until the contact resistance becomes smaller than the threshold value or the electrode terminals 31 come into good contact with the scalp. In this way, the biosignal detecting device 101 automatically brings the electrode terminals 31 into good contact with the scalp.

The present disclosure is not restricted by the embodiments mentioned above but may be modified and changed variously within the scope thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A biosignal detecting electrode which comprises a rotary part which is rotatably attached on a brace mountable on a living body and has a first side that joins to said brace and a second side opposite to said first side, a plurality of electrode terminals attached to said rotary part in such a way that they obliquely project from said second side of said rotary part, a drive mechanism configured to rotate said rotary part, a signal processing unit configured to measure an electrical resistance, which is a contact resistance of the plurality of electrode terminals, and a control unit configured to control said drive mechanism to rotate the rotary part in response to the contact resistance which is detected at said plurality of electrode terminals, wherein the signal processing unit is configured to repeatedly measure the contact resistance of the plurality of electrode terminals and the control unit is configured to repeatedly cause the drive mechanism to rotate the rotary part until the contact resistance meets a threshold.

2. The biosignal detecting electrode as defined in claim 1, in which said rotary part is capable of rotation around a straight line passing through a center of said first side and a center of said second side, said electrode terminals are arranged rotationally symmetrical with respect to the straight line passing through the center of said first side and the center of said second side, and said electrode terminals project over an exactly or approximately equal distance from said first side.

3. The biosignal detecting electrode as defined in claim 2, in which said electrode terminals are made of liquid holding material impregnated with an electrolytic solution.

4. The biosignal detecting electrode as defined in claim 3, in which said electrode terminals are made of elastic material.

5. A biosignal detecting device which comprises a brace to be mounted on a living body, a rotary part which is rotatably mounted on said brace and has a first side that joins to said brace and a second side opposite to said first side, a plurality of electrode terminals which project obliquely with respect to said second side of said rotary part, a drive mechanism configured to rotate said rotary part, a signal processing unit configured to measure an electrical resistance, which is a contact resistance of the plurality of electrode terminals, and a control unit configured to control said drive mechanism to rotate the rotary part in response to the contact resistance which is detected at said electrode tetininals, wherein the signal processing unit is configured to repeatedly measure the contact resistance of the plurality of electrode terminals and the control unit is configured to repeatedly cause the drive mechanism to rotate the rotary part until the contact resistance meets a threshold.

6. The biosignal detecting device as defined in claim 5 comprised of at least a parietal electrode, an occipital electrode, a right electro-ocular electrode, a left electro-ocular electrode, a left reference electrode, a right reference electrode and a signal processing unit.

7. The biosignal detecting device as defined in claim 6 where the signal processing unit is comprised of at least an operational amplifier connected to the parietal electrode, the occipital electrode, the right electro-ocular electrode, the left electro-ocular electrode, the right reference electrode and the left reference electrode; a filter; an A/D converter; an analyzer and a memory.

8. The biosignal detecting device as defined in claim 3, in which said electrode terminals have a core made of a stiff material.

9. The biosignal detecting device as defined in claim 8, in which said stiff material includes at least one of a metal and a plastic.

* * * * *